United States Patent
Yun et al.

(10) Patent No.: US 9,243,270 B2
(45) Date of Patent: Jan. 26, 2016

(54) METHOD FOR PRODUCING METABOLITES FROM OMEPRAZOLE USING BACTERIAL CYTOCHROME P450, AND COMPOSITION FOR SAME

(71) Applicant: Chul-Ho Yun, Yuseong-gu, Daejeon (KR)

(72) Inventors: Chul-Ho Yun, Daejeon (KR); Sang-Hoon Ryu, Gwangju (KR); Hyung-Sik Kang, Gwangju (KR)

(73) Assignee: Chul-Ho Yun, Daejeon (KR)

( * ) Notice: Subject to any disclaimer, the term of this patent is extended or adjusted under 35 U.S.C. 154(b) by 0 days.

(21) Appl. No.: 14/375,522

(22) PCT Filed: Dec. 21, 2012

(86) PCT No.: PCT/KR2012/011295
§ 371 (c)(1),
(2) Date: Nov. 18, 2014

(87) PCT Pub. No.: WO2013/115484
PCT Pub. Date: Aug. 8, 2013

(65) Prior Publication Data
US 2015/0093793 A1    Apr. 2, 2015

(30) Foreign Application Priority Data

Jan. 31, 2012 (KR) .................. 10-2012-0009300

(51) Int. Cl.
| | | |
|---|---|---|
| *C12P 17/10* | (2006.01) | |
| *C12N 9/02* | (2006.01) | |
| *C12N 9/04* | (2006.01) | |
| *C07H 21/04* | (2006.01) | |
| *C12P 17/16* | (2006.01) | |

(52) U.S. Cl.
CPC ............. *C12P 17/165* (2013.01); *C12N 9/0042* (2013.01); *C12N 9/0071* (2013.01); *C12Y 114/14001* (2013.01)

(58) Field of Classification Search
None
See application file for complete search history.

(56) References Cited

FOREIGN PATENT DOCUMENTS

| KR | 10-2010-0063486 A | 6/2010 |
| KR | 10-2011-0020525 A | 3/2011 |
| KR | 10-2011-0086686 A | 7/2011 |

OTHER PUBLICATIONS

GenBank Accession No. ADA57059, "NADPH-Cytochrome P450 Reductase 102A1V3 [*Bacillus megaterium*]", Mar. 25, 2011—See the entire document.
Abelo A. et al, "Stereoselective Metabolism of Omeprazole by Human Cytochrome P450 Enzymes", Drug Metab. Dispos., Aug. 2000, vol. 28, No. 8, pp. 966-972. See the entire document.
Yun, Chul-Ho et al., "The Bacterial P450 BM3: A Prototype for a Biocatalyst with Human P450 Activities", Trends in Biotechnology, Mar. 29, 2007, vol. 25, No. 7, pp. 289-298. See the entire document.

*Primary Examiner* — Iqbal H Chowdhury
(74) *Attorney, Agent, or Firm* — Sughrue Mion, PLLC

(57) ABSTRACT

The present invention relates to a novel method for producing metabolites from omeprazole using bacterial cytochrome P450, and a composition therefor, and more specifically, to a composition and a kit for producing a 5'-hydroxyl product from omeprazole, containing bacterial cytochrome P450 BM3 (CYP102A1) or mutants thereof, and to a method for producing the same. The composition, the kit, and the method are capable of economically and highly efficiently mass-producing the 5'-hydroxyl product from the omeprazole, and thus will significantly contribute to development of a novel drug using metabolites from the omeprazole.

7 Claims, 14 Drawing Sheets

FIG. 1

| | |
|---|---|
| 1 | MTIKEMPQPKTFGELKNLPLLNTDKPVQALMKIADELGEIFKFEAPGRVTRYLSSQRLIK |
| 61 | EACDESRFDKNLSQALKFVRDFAGDGLFTSWTHEKNWKKAHNILLPSFSQGAMKGYHAMM |
| 121 | VDIAVQLVQKWERLNADEHIEVPEDMTRLTLDTIGLCGFNYRFNSFYRDQPHPFITSMVR |
| 181 | ALDEAMNKLQRANPDDPAYDENKRQFQEDIKVMNDLVDKIIADRKASGEQSDDLLTHMLN |
| 241 | GKDPETGEPLDDENIRYQIITFLIAGHETTSGLLSFALYFLVKNPHVLQKAAEEAARVLV |
| 301 | DPVPSYKQVKQLKYVGMVLNEALRLWPTAPAFSLYAKEDTVLGGEYPLEKGDELMVLIPQ |
| 361 | LHRDKTIWGDDVEEFRPERFENPSAIPQHAFKPFGNGQRACIGQQFALHEATLVLGMMLK |
| 421 | HFDFEDHTNYELDIKETLTLKPEGFVVKAKSKKIPLGGIPSPSTEQSAKKVRKKAENAHN |
| 481 | TPLLVLYGSNMGTAEGTARDLADIAMSKGFAPQVATLDSHAGNLPREGAVLIVTASYNGH |
| 541 | PPDNAKQFVDWLDQASADEVKGVRYSVFGCGDKNWATTYQKVPAFIDETLAAKGAENIAD |
| 601 | RGEADASDDFEGTYEEWREHMWSDVAAYFNLDIENSEDNKSTLSLQFVDSAADMPLAKMH |
| 661 | GAFSTNVVASKELQQPGSARSTRHLEIELPKEASYQEGDHLGVIPRNYEGTVNRVTAREG |
| 721 | LDASQQIRLEAEEEKLAHLPLAKTVSVEELLQYVELQDPVTRTQLRAMAAKTVCPPHKVE |
| 781 | LEALLEKQAYKEQVLAKRLTMLELLEKYPACEMKFSEFIALLPSIRPRYYSISSSPRVDE |
| 841 | KQASITVSVVSGEAWSGYGEYKGIASNYLAELQEGDTITCFISTPQSEFTLPKDPETPLI |
| 901 | MVGPGTGVAPFRGFVQARKQLKEQGQSLGEAHLYFGCRSPHEDYLYQEELENAQSEGIIT |
| 961 | LHTAFSRMPNQPKTYVQHVMEQDGKKLIELLDQGAHFYICGDGSQMAPAVEATLMKSYAD |
| 1021 | VHQVSEADARLWLQQLEEKGRYAKDVWAG- |

FIG. 2

```
5'-ATGACAATTAAAGAAATGCCTCAGCCAAAAACGTTTGGAGAGCTTAAAAATTTACCGTTATTA
AACACAGATAAACCGGTTCAAGCTTTGATGAAAATTGCGGATGAATTAGGAGAAATCTTTAAA
TTCGAGGCGCCTGGTCGTGTAACGCGCTACTTATCAAGTCAGCGTCTAATTAAAGAAGCATGC
GATGAATCACGCTTTGATAAAAACTTAAGTCAAGCGCTTAAATTTGTACCTGATTTTGCAGGA
GACGGGTTATTTACAAGCTGGACGCATGAAAAAAATTGGAAAAAAGCGCATAATATCTTACTT
CCAAGCTTCAGTCAGCAGGCAATGAAAGGCTATCATGCGATGATGGTCGATATCGCCGTGCAG
CTTGTTCAAAAGTGGGAGCGTCTAAATGCAGATGAGCATATTGAAGTACCGGAAGACATGACA
CGTTTAACGCTTGATACAATTGGTCTTTGCGGCTTTAACTATCGCTTTAACAGCTTTTACCGA
GATCAGCCTCATCCATTTATTACAAGTATGGTCCGTGCACTGGATGAAGCAATGAACAAGCTG
CAGCGAGCAAATCCAGACGACCCAGCTTATGATGAAAACAAGCGCCAGTTTCAAGAAGATATC
AAGGTGATGAACGACCTAGTAGATAAAATTATTGCAGATCGCAAAGCAAGCGGTGAACAAAGC
GATGATTTATTAACGCATATGCTAAACGGAAAAGATCCAGAAACGGGTGAGCCGCTTGATGAC
GAGAACATTCGCTATCAAATTATTACATTCTTAATTGCGGGACACGAAACAACAAGTGGTCTT
TTATCATTTGCGCTGTATTTCTTAGTGAAAAATCCACATGTATTACAAAAAGCAGCAGAAGAA
GCAGCACGAGTTCTAGTAGATCCTGTTCCAAGCTACAAACAAGTCAAACAGCTTAAATATGTC
GGCATGGTCTTAAACGAAGCGCTGCGCTTAGCCCAACTGCTCCTGCGTTTTCCCTATATGCA
AAAGAAGATACGGTGCTTGGAGGAGAATATCCTTTAGAAAAAGGCGACGAACTAATGGTTCTG
ATTCCTCAGCTTCACCGTGATAAAACAATTTGGGGAGACGATGTGGAAGAGTTCCGTCCAGAG
CGTTTTGAAAATCCAAGTGCGATTCCGCAGCATGCGTTTAAACCGTTTGGAAACGGTCAGCGT
GCGTGTATCGGTCAGCAGTTCGCTCTTCATGAAGCAACGCTGGTACTTGGTATGATGCTAAAA
CACTTTGACTTTGAAGATCATACAAACTACGAGCTCGATATTAAAGAAACTTTAACGTTAAAA
CCTGAAGGCTTTGTGGTAAAAGCAAAATCGAAAAAAATTCCGCTTGGCGGTATTCCTTCACCT
AGCACTGAACAGTCTGCTAAAAAAGTACGCAAAAAGGCAGAAAACGCTCATAATACGCCGCTG
CTTGTGCTATACGGTTCAAATATGGGAACAGCTGAAGGAACGGCGCGTGATTTAGCAGATATT
GCAATGAGCAAAGGATTTGCCACCGCAGGTCGCAACGCTTGATTCACACGCCGGAAATCTTCCG
CGCGAAGGAGCTGTATTAATTGTAACGGCGTCTTATAACGGTCATCCGCCTGATAACGCAAAG
CAATTTGTCGACTGGTTAGACCAAGCGTCTGCTGATGAAGTAAAAGGCGTTCGCTACTCCGTA
TTTGGATGCGGCGATAAAAACTGGGCTACTACGTATCAAAAAGTGCCTGCTTTTATCGATGAA
ACGCTTGCCGCTAAAGGGGCAGAAAACATCGCTGACCGCGGTGAAGCAGATGCAAGCGACGAC
TTTGAAGGCACATATGAAGAATGGCGTGAACATATGTGGAGTGACGTAGCAGCCTACTTTAAC
CTCGACATTGAAAACAGTGAAGATAATAAATCTACTCTTTCACTTCAATTTGTCGACAGCGCC
GCGGATATGCCGCTTGCGAAAATGCACGGTGCGTTTTCAACGAACGTCGTAGCAAGCAAAGAA
CTTCAACAGCCAGGCAGTGCACGAAGCACGCGACATCTTGAAATTGAACTTCCAAAAGAAGCT
TCTTATCAAGAAGGAGATCATTTAGGTGTTATTCCTCGCAACTATGAAGGAATAGTAAACCGT
GTAACAGCAAGGTTCGGCCTAGATGCATCACAGCAAATCCGTCTGGAAGCAGAAGAAGAAAAA
TTAGCTCATTTGCCACTCGCTAAAACAGTATCCGTAGAAGAGCTTCTGCAATACGTGGAGCTT
CAAGATCCTGTTACGCGCACGCAGCTTCGCGCAATGGCTGCTAAAACGGTCTGCCCGCCGCAT
AAAGTAGAGCTTGAAGCCTTGCTTGAAAAGCAAGCCTACAAAGAACAAGTGCTGGCAAAACGT
TTAACAATGCTTGAACTGCTTGAAAAATACCCGGCGTGTGAAATGAAATTCAGCGAATTTATC
GCCCTTCTGCCAAGCATACGCCCGCGCTATTACTCGATTTCTTCATCACCTCGTGTCGATGAA
AAACAAGCAAGCATCACGGTCAGCGTTGTCTCAGGAGAAGCGTGGAGCGGATATGGAGAATAT
AAAGGAATTGCGTCGAACTATCTTGCCGAGCTGCAAGAAGGAGATACGATTACGTGCTTTATT
TCCACACCGCAGTCAGAATTTACGCTGCCAAAAGACCCTGAAACGCCGCTTATCATGGTCGGA
CCGGGAACAGGCGTCGCGCCGTTTAGAGGCTTTGTGCAGGCGCGCAAACAGCTAAAAGAACAA
GGACAGTCACTTGGAGAAGCACATTTATACTTCGGCTGCCGTTCACCTCATGAAGACTATCTG
TATCAAGAAGGCTTGAAAACGCCCAAAGCGAAGGCATCATTACGCTTCATACCGCTTTTTCT
CGCATGCCAAATCAGCCGAAAACATACGTTCAGCACGTAATGGAACAAGACGGCAAGAAATTG
ATTGAACTTCTTGATCAAGGAGCGCACTTCTATATTTGCGGAGACGGAAGCCAAATGGCACCT
GCCGTTGAAGCAACGCTTATGAAAAGCTATGCTGACGTTCACCAAGTGAGTGAAGCAGACGCT
CGCTTATGGCTGCAGCAGCTAGAAGAAAAAGGCCGATACGCAAAAGACGTGTGGGCTGGGTAA-3'
```

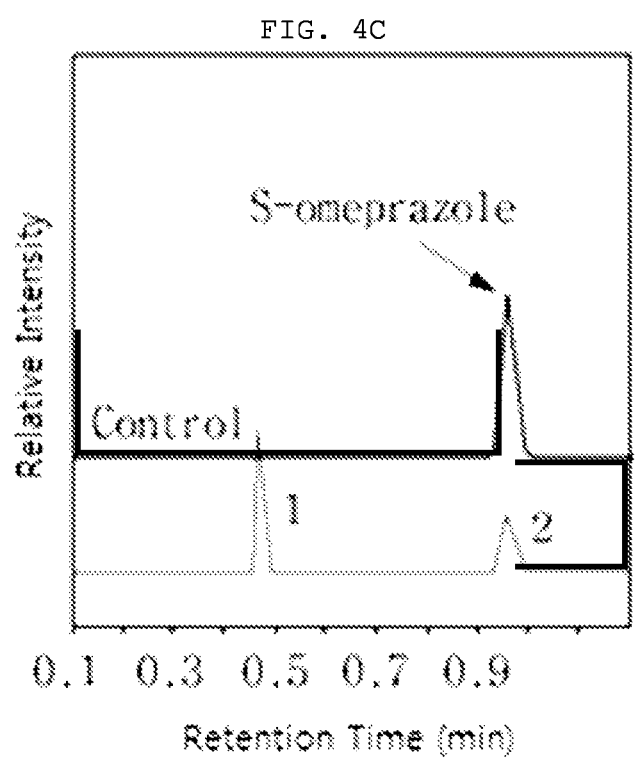

METHOD FOR PRODUCING METABOLITES FROM OMEPRAZOLE USING BACTERIAL CYTOCHROME P450, AND COMPOSITION FOR SAME

CROSS REFERENCE TO RELATED APPLICATIONS

This application is a National Stage of International Application No. PCT/KR2012/011295, filed on Dec. 21, 2012, which claims priority from Korean Patent Application No. 10-2012-0009300, filed on Jan. 31, 2012, the contents of all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jul. 25, 2014, is named Q213529_SL.txt and is 35,598 bytes in size.

TECHNICAL FIELD

The present invention relates to a novel method for producing metabolites from omeprazole using bacterial cytochrome P450 and a composition therefor, and more specifically, to a composition and a kit for producing a 5'-hydroxyl product from omeprazole, containing bacterial cytochrome P450 BM3 (CYP102A1) or mutants thereof, and a method for producing the same.

BACKGROUND ART

Omeprazole, which is a proton pump inhibitor, is known as a therapeutic agent of indigestion, stomach ulcer, gastroesophageal reflux disease and laryngopharyngeal reflux disease. The omeprazole, which is a racemate, contains S and R enantiomers at a ratio of 50:50. Both enantiomers in the above acidic condition are converted into an achiral compound and reacted with a cysteine group of H+/K+ATPase to inhibit stomach acid production in a parietal cell of the stomach. The omeprazole and enantiomers are metabolized by CYP2C19 and CYP3A4 which are cytochrome P450 present in a human liver, and main metabolites thereof include 5'-O-desmethyl omeprazole, 5'- and 3'-hydroxyomeprazole and omeprazole sulfone (see Renberg et al., Drug Metab Dispos 17:69-76, 1989; Andersson et al., Clin Pharmacokinet 40:411-426, 2001, Li et al., J Pharmacol Exp Ther 315:777-787, 2005). It has been reported that the R enantiomer is generally metabolized to be 5'-O-desmethyl omeprazole, 5'-hydroxyomeprazole by CYP2C19 and the S enantiomer is generally metabolized to be omeprazole sulfone, 3'-hydroxyomeprazole by CYP3A4.

Cytochrome P450 (P450 or CYP) enzyme is a large family consisting of enzymes serving as catalysts of significantly various oxidation reactions throughout the nature ranging from archaea to bacteria, fungi, plants, animals and human. Due to variety of catalytic function, and a wide range of substrates thereof, P450s are largely useful as a biological catalyst in production of fine chemicals including medical supplies, and the like (see Guengerich, Nat Rev Drug Discov 1:359-366, 2002; Urlacher et al., Trends Biotechnol 24:324-330, 2006; Yun C H et al., Trends Biotechnol 25:289-298, 2007; Lamb et al., Curr Opin Biotechnol 18:504-512, 2007). However, despite of potential usability of the cytochrome P450 enzymes of a mammal in various biotechnological fields as described above, P450s have low stability, catalytic activity, and availability, and thus, are not appropriate as a biological catalyst.

When a prodrug is converted into a biologically "active metabolite" by P450s by humans during development of the drug (see Johnson et al., Breast Cancer Res. Treat 85:151-159, 2004), a large amount of pure metabolites are required for a research of efficacy, toxicity, pharmacokinetics, and the like, of the drug. In addition, when the metabolite itself has a biological activity, direct administration of the metabolite in vivo has a large benefit, and thus, mass-production of the metabolite is important.

When the omeprazole is administered into a human body, since the omeprazole is metabolized by CYP2C19 and CYP3A4, a rate at which the metabolite is produced may vary depending on the degree of expression of the enzymes. In addition, a drug interaction problem with other drugs metabolized by the enzymes occurs. Therefore, when the omeprazole metabolite is directly used as a drug, the drug interaction problem may be avoided.

However, since there are various problems in chemically synthesizing pure metabolites, in order to product a metabolite of a drug or a drug candidate as an alternative of the metabolite chemical synthesis, P450 is used. The production of the metabolites using human P450s expressed from E. coli (see Yun et al., Curr Drug Metab 7:411-429, 2006) or insect cells (see Rushmore et al., Metab Eng 2:115-125, 2000; Vail et al., J Ind Microbiol Biotechnol 32:67-74, 2005) has been reported. However, these systems have problems such as expensive cost and low productivity due to limited stability, slow reaction rate, and the like (see Guengerich et al., Crit Rev Toxicol 26:551-583, 1996). Accordingly, a method for using engineered bacterial P450 enzymes having a desired catalytic activity as an alternative for producing metabolites in human has been suggested (see Yun C H et al., Trends Biotechnol 25:289-298, 2007).

Meanwhile, heme domain of P450 BM3 (CYP102A1) derived from Bacillus megaterium has a mono oxygenase activity, which is significantly similar to a member of mammalian of CYP4A (fatty acid hydroxylase) family. Naturally, it is formed of single polypeptides in which a CYP102A1 reductase domain having a mammal-like diflavin reductase function is fused to a C-terminal of the P450 heme domain. The fusion of two enzyme activities makes a fusible CYP102A1 to be a desirable mammal model, in particular, a desirable model of a human P450 enzyme. It has been reported that CYP102A1 mutants genetically engineered through logical design or directed evolution oxidize several substrates of human P450 to product a metabolite having higher activity (see Kim et al., Drug Metab Dispos 36:2166-2170, 2008, Kim et al., Drug Metab Dispos 37:932-936, 2009, Kim et al., J Mol Catal B: Enzym 63:179-187, 2010; Otey et al., Biotechnol Bioeng 93:494-499, 2006; Yun C H et al., Trends Biotechnol 25:289-298, 2007).

Based on the above-description, it has been suggested that the mutants of CYP102A1 may be developed as a biological catalyst for detection and synthesis of the drug. Recently, it has been reported that several selected mutants may allow the CYP102A1 enzyme to product a metabolite in human as a drug (see Kim et al., Drug Metab Dispos 36:2166-2170, 2008, Kim et al., Drug Metab Dispos 37:932-936, 2009); however, a method for biologically producing a metabolite in human from the omeprazole has not been reported yet.

DISCLOSURE

Technical Problem

An object of the present invention is to provide an enzyme capable of more stably and effectively performing a catalyst function in a selective conversion reaction into a 5'-hydroxyl product by oxidizing omeprazole.

In addition, another object of the present invention is to provide a composition for producing a 5'-hydroxyl product from omeprazole, containing the enzyme.

Further, another object of the present invention is to provide a method for producing a 5'-hydroxyl product from omeprazole, including reacting the enzyme with the omeprazole.

In addition, another object of the present invention is to provide a kit for producing a 5'-hydroxyl product from omeprazole, containing the enzyme and an NADPH-generating system.

Technical Solution

In one general aspect, the present invention provides at least one enzyme selected from the group consisting of a wild-type CYP102A1 and mutants of CYP102A1.

The enzyme may stably and effectively perform a catalyst function in a selective conversion reaction into a 5'-hydroxyl product by oxidizing omeprazole.

In another general aspect, the present invention provides a method for selective mass-production of a metabolite in human, in particular, 5'-hydroxyl product, from omeprazole, using a wild-type CYP102A1 and mutants of CYP102A1 which is a bacterial P450 enzyme, and a composition and a kit therefor.

The wild-type CYP102A1 and the mutants of CYP102A1 according to the present invention may be used as a catalyst in an oxidation reaction using omeprazole as a substrate, the omeprazole known as a substrate of human P450, and in particular, the omeprazole metabolite produced when using human CYP2C19 as a catalyst includes two kinds of metabolites; meanwhile, when using the bacterial CYP102A1 or the mutants thereof according to the present invention as a catalyst, the 5'-hydroxyl product may be selectively produced.

In a preferred exemplary embodiment of the present invention, the present inventors confirmed that when the bacterial wild-type CYP102A1 and site-directed mutants thereof were mass-expressed in *E. coli* (see Tables 1 and 2), and the omeprazole was reacted with an NADPH-generating system, the omeprazole was converted into the metabolite in human by HPLC (see FIGS. 3, 4 and 5) and LC-MS spectrum (see FIG. 6). It was confirmed in human CYP2C19, omeprazole was oxidized to produce two kinds of main metabolites, that is, 3'-hydroxyomeprazole and 5'-hydroxyomeprazole; however, in the bacterial wide-type CYP102A1 and the mutants thereof, one main product was selectively produced, which was 5'-hydroxyomeprazole.

The wild-type CYP102A1 with respect to the production of the product, 17 kinds of mutants and 6 kinds of mutant chimeras had variously wide range of molecular catalytic activity (turnover number) (see FIG. 5). It was confirmed that in the mutant #10 showing high activity in the total molecular catalytic activity, the highest activity was shown in the reaction at 1 mM concentration (A) of the omeprazole for 2 to 4 hours (B); meanwhile, in the wild-type CYP102A1 enzyme, the activity with respect to the omeprazole was hardly shown (see FIG. 7).

Based on the examination result as described above, in another general aspect, the present invention provides a composition for producing a 5'-hydroxyl product from omeprazole, containing at least one enzyme selected from the group consisting of a wild-type CYP102A1 and mutants of CYP102A1, wherein the mutant of CYP102A1 has a sequence modified by at least one selected from the group consisting of substitution of 48th amino acid arginine (R) with an amino acid selected from the group consisting of alanine, valine, leucine, isoleucine, proline, methionine, phenylalanine and tryptophan, substitution of 52nd amino acid tyrosine (Y) with an amino acid selected from the group consisting of alanine, valine, isoleucine, proline, methionine, phenylalanine, and tryptophan, substitution of 65th amino acid glutamic acid (E) with an amino acid selected from the group consisting of glycine, serine, threonine, cysteine, tyrosine, asparagine and glutamine, substitution of 75th amino acid alanine (A) with an amino acid selected from the group consisting of glycine, serine, threonine, cysteine, tyrosine, asparagine, and glutamine, substitution of 82nd amino acid phenylalanine (F) with an amino acid selected from the group consisting of alanine, valine, leucine, isoleucine, proline, methionine and tryptophan, substitution of 87th amino acid leucine (L) with an amino acid selected from the group consisting of alanine, valine, isoleucine, proline, methionine, phenylalanine and tryptophan, substitution of 88th amino acid phenylalanine (F) with an amino acid selected from the group consisting of alanine, valine, leucine, isoleucine, proline, methionine and tryptophan, substitution of 144th amino acid glutamic acid (E) with an amino acid selected from the group consisting of glycine, serine, threonine, cysteine, tyrosine, asparagine, and glutamine, substitution of 189th amino acid leucine (L) with an amino acid selected from the group consisting of glycine, serine, threonine, cysteine, tyrosine, asparagine, and glutamine, and substitution of 268th amino acid glutamic acid (E) with an amino acid selected from the group consisting of alanine, valine, leucine, isoleucine, proline, methionine, phenylalanine and tryptophan, of the wild-type CYP102A1 represented by an amino acid of SEQ ID NO: 16.

The omeprazole may be a racemate containing S- or R-omeprazole which is an enantiomer, or an enantiomer of the S- and R-omeprazole at a ratio of 50:50, but the present invention is not limited thereto.

In another general aspect, the present invention provides a method for producing a 5'-hydroxyl product from omeprazole, including reacting omeprazole with at least one enzyme selected from the group consisting of a wild-type CYP102A1 and mutants of CYP102A1.

In the method for producing the 5'-hydroxyl product, the mutant of CYP102A1 may preferably have a sequence modified by at least one selected from the group consisting of substitution of 48th amino acid arginine (R) with an amino acid selected from the group consisting of alanine, valine, leucine, isoleucine, proline, methionine, phenylalanine and tryptophan, substitution of 52nd amino acid tyrosine (Y) with an amino acid selected from the group consisting of alanine, valine, isoleucine, proline, methionine, phenylalanine, and tryptophan, substitution of 65th amino acid glutamic acid (E) with an amino acid selected from the group consisting of glycine, serine, threonine, cysteine, tyrosine, asparagine and glutamine, substitution of 75th amino acid alanine (A) with an amino acid selected from the group consisting of glycine, serine, threonine, cysteine, tyrosine, asparagine, and glutamine, substitution of 82nd amino acid phenylalanine (F) with an amino acid selected from the group consisting of alanine, valine, leucine, isoleucine, proline, methionine and tryptophan, substitution of 87th amino acid leucine (L) with an amino acid selected from the group consisting of alanine, valine, isoleucine, proline, methionine, phenylalanine and tryptophan, substitution of 88th amino acid phenylalanine (F) with an amino acid selected from the group consisting of alanine, valine, leucine, isoleucine, proline, methionine and tryptophan, substitution of 144th amino acid glutamic acid (E) with an amino acid selected from the group consisting of glycine, serine, threonine, cysteine, tyrosine, asparagine, and glutamine, substitution of 189th amino acid leucine (L) with an amino acid selected from the group consisting of glycine, serine, threonine, cysteine, tyrosine, asparagine, and glutamine, and substitution of 268th amino acid glutamic acid (E) with an amino acid selected from the group consisting of alanine, valine, leucine, isoleucine, proline, methionine, phenylalanine and tryptophan, of the wild-type CYP102A1 represented by an amino acid of SEQ ID NO: 16.

In the present invention, the production of the mutants of CYP102A1 may be performed by any known mutation method known in the art, such as a deletion-mutation method (see Kowalski D. et al., *J. Biochem.*, 15, 4457), a PCT method, a Kunkel method, a site-directed mutation method, DNA shuffling, a staggered extension process (StEP), error-prone PCR, and the like.

In the mutant of CYP102A1 of the present invention, the amino acid of wild-type CYP102A1 protein represented by SEQ ID NO: 16, has a sequence modified by natural or artificial substitution, deletion, addition and/or insertion. Preferably, the substituted amino acid may be substituted while having similar properties to an amino acid to be substituted as classified below. For example, alanine, valine, leucine, isoleucine, proline, methionine, phenylalanine and tryptophan are classified into all non-polar amino acids and have similar properties to each other. Examples of non-charged amino acid may include glycine, serine, threonine, cysteine, tyrosine, asparagine, glutamine, and the like, examples of acidic amino acid may include aspartic acid and glutamic acid, and examples of basic amino acid may include lysine, arginine, and histidine.

The mutant of CYP102A1 of the present invention includes polypeptide including amino acid sequences having at least 50% identity, preferably, at least 75% identity, and more preferably, at least 90% identity, with CYP102A1 protein sequence represented by SEQ ID NO: 16.

The desirable mutant of the wild-type CYP102A1 may include at least one selected from the group consisting of substitution of 48th amino acid arginine (R) with leucine (L), substitution of 52nd amino acid tyrosine (Y) with phenylalanine (F), substitution of 65th amino acid glutamic acid (E) with glycine (G), substitution of 75th amino acid alanine (A) with glycine (G), substitution of 82nd amino acid phenylalanine (F) with isoleucine (I), substitution of 87th amino acid leucine (L) with isoleucine (I), substitution of 88th amino acid phenylalanine (F) with valine (V), substitution of 144th amino acid glutamic acid (E) with glycine (G), substitution of 189th amino acid leucine (L) with glutamine (Q), and substitution of 268th amino acid glutamic acid (E) with valine (V), of the wild-type CYP102A1 represented by SEQ ID NO: 16.

In the most preferred mutant of CYP102A1, a substituted position and a substituted amino acid of the wild-type CYP102A1 amino acid represented by SEQ ID NO: 16 may be selected from the group consisting of F88A, R48L/Y52F, A75G/F88V/L189Q, R48L/L87I/L189Q, R48L/F88V/L189Q, R48L/F88V/L189Q/E268V, R48L/L87I/L189Q/E268V, R48L/L87I/F88V/L189Q, R48L/F88V/E144G/L189Q/E268V, R48L/E65G/F88V/E144G/L189Q/E268V, R48L/F82I/F88V/E144G/L189Q/E268V and R48L/E65G/F82I/F88V/E144G/L189Q/E268V.

The protein of the present invention may be produced by well-known methods in the art, for example, a peptide synthesis method (Merrifield, J. Am. Chem. Soc., 85: 2149-2154, 1963 reference) using genetic engineering technique, solid-phase technique, or a method for cutting the protein of the present invention by a suitable peptidase, and the like. The protein of the present invention may be produced as a natural protein, or may be produced by a recombination method for culturing a cell transformed to be DNA encoding CYP102A1 or the mutant thereof and recovering the transformed cell. The protein of the present invention may be produced by inserting a nucleic acid molecule encoding the protein of the present invention into a suitable expression vector, culturing a transformant produced by delivering the vector to an appropriate cell, and purifying the protein expressed by the transformant.

The vector may have, for example, plasmid, cosmid, viral particle, or phage form. Example of a host cell cloning or expressing DNA in the vector may include a prokaryotic cell, yeast and a higher eukaryotic cell. Culturing conditions such as medium, temperature, pH, and the like, may be appropriately selected without excessive experiments by a person skilled in the art. In general, principle, protocol, technique for maximizing productivity of cell culturing may be used with reference to Mammalian Cell Biotechnology: a Practical Approach, M. Butler, ed. (IRL Press, 1991).

The expression and cloning vector may generally contain a promoter operably connected to a nucleic acid sequence encoding CYP102A1 inducing mRNA synthesis or the mutants thereof. Various promoters recognized by the host cell are known. Examples of the promoter appropriate for being used in prokaryotic hosts include a $\beta$-lactamase and lactose promoter system, alkaline phosphatase, a tryptophan promoter system, and a hybrid promoter, for example, a tac promoter. In addition, a promoter used in a bacterial system may contain Shine-Dalgarno (S.D.) sequence operably connected to DNA encoding SISP-1. Examples of the promoter sequence appropriate for being used in a yeast host may include 3-phosphoglycerate kinase or other glycolytic enzymes.

The method for producing a 5'-hydroxyl product from omeprazole may further include: adding an NADPH-generating system.

In another general aspect, the present invention provides a kit for producing a 5'-hydroxyl product from omeprazole, containing an NADPH-generating system and at least one enzyme selected from the group consisting of a wild-type CYP102A1 and mutants of CYP102A1.

In the mutant of CYP102A1, a substituted position and a substituted amino acid of the wild-type CYP102A1 amino acid represented by an amino acid sequence of SEQ ID NO: 16 may preferably be at least one selected from the group consisting of F88A, R48L/Y52F, A75G/F88V/L189Q, R48L/L87I/L189Q, R48L/F88V/L189Q, R48L/F88V/L189Q/E268V, R48L/L87I/L189Q/E268V, R48L/L87I/F88V/L189Q, R48L/F88V/E144G/L189Q/E268V, R48L/E65G/F88V/E144G/L189Q/E268V, R48L/F82I/F88V/E144G/L189Q/E268V and R48L/E65G/F82I/F88V/E144G/L189Q/E268V, but the present invention is not limited thereto. In addition, the kit may further contain a reagent required for performing the reaction.

The NADPH-generating system may contain glucose 6-phosphate, NADP$^+$ and yeast glucose-6-phosphate dehydrogenase, but the present invention is not limited thereto.

The CYP102A1 or the mutants thereof are a bacterial enzyme capable of stably and effectively performing the catalyst function in selective conversion reaction into a 5'-hydroxyl product by oxidizing omeprazole known as a substrate of human P450, and thus, may be effectively used for biologically producing metabolites in human from the omeprazole.

Advantageous Effects

The bacterial wild-type CYP102A1 and the mutants thereof according to the present invention may more stably and effectively perform the catalyst function in the conversion reaction from omeprazole into a 5'-hydroxyl product to be capable of environmentally friendly and selectively mass-producing the 5'-hydroxyl product. The composition, the kit, and the method for producing the 5'-hydroxyl product according to the present invention may include the bacterial wild-type CYP102A1 and the mutants thereof to be capable of economically and highly efficiently mass-producing the 5'-hydroxyl product from the omeprazole, and thus will significantly contribute to development of a novel drug using metabolites from the omeprazole.

DESCRIPTION OF DRAWINGS

The above and other objects, features and advantages of the present invention will become apparent from the following description of preferred embodiments given in conjunction with the accompanying drawings, in which:

FIG. 1 shows an amino acid sequence of a wild-type CYP102A1 (SEQ ID NO: 16) according to the present invention.

FIG. 2 shows a base sequence of a wild-type CYP102A1 (SEQ ID NO: 17) according to the present invention.

BEST MODE

Figure 3A:
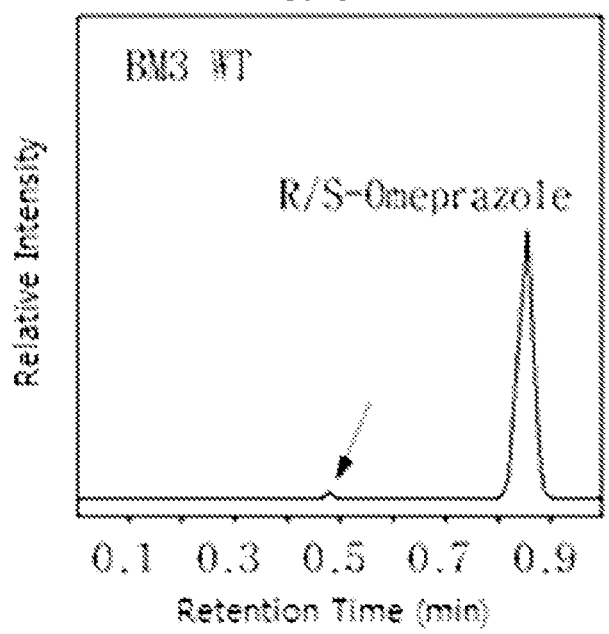
FIG. 3 shows HPLC chromatogram (UV absorbance measured at 302 nm) of an omeprazole metabolite produced by a wild-type CYP102A1 and mutants thereof according to the present invention (Peak: confirmed by peaks of the metabolites produced by human CYP2C19 with respect to retention time; Arrow: indication of substrate and 5'-hydroxyl product which is a main product): (A) wild-type (WT), (B) M#10, (C) M#11, (D) M#12, (E) M#13, (F) M#14, (G) M#15, (H) M#16 and (I) M#17.
Figure 3B:
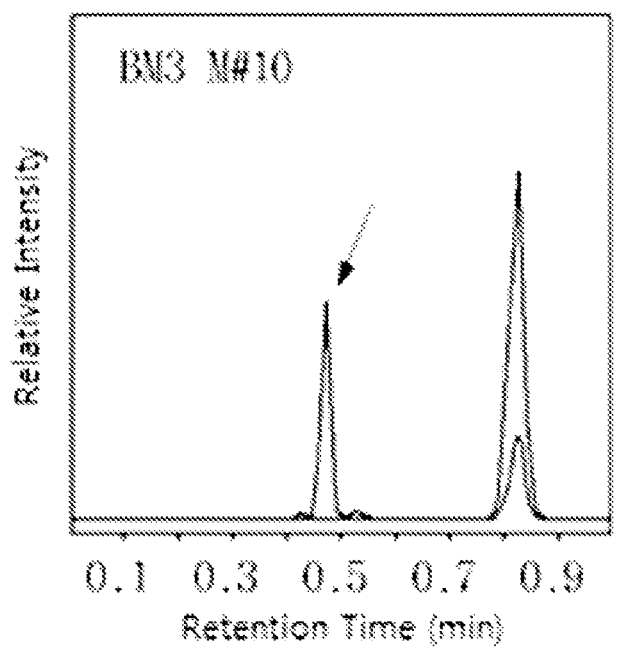
Figure 3C:
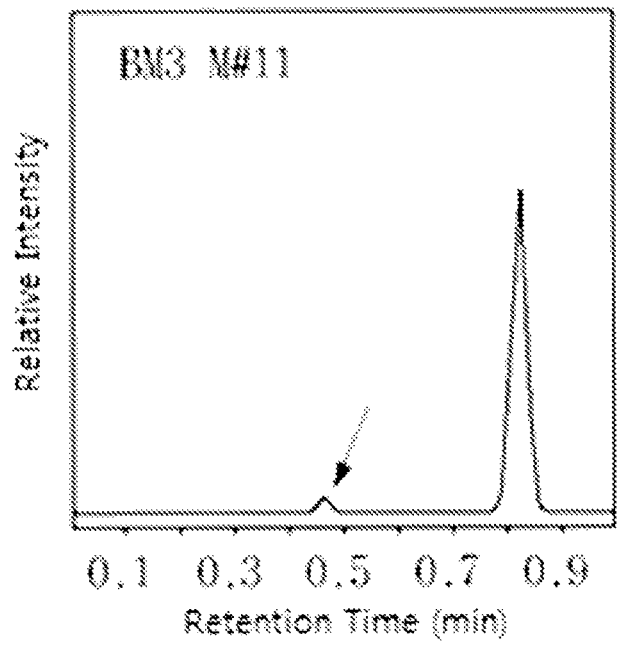
Figure 3D:
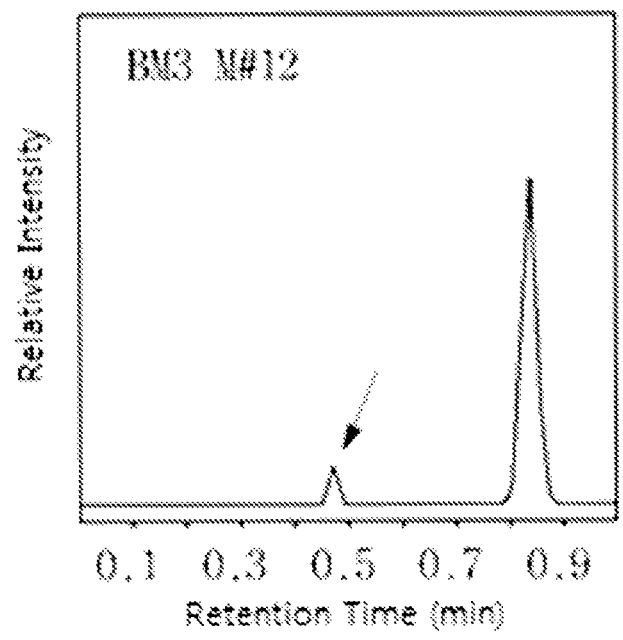
Figure 3E:
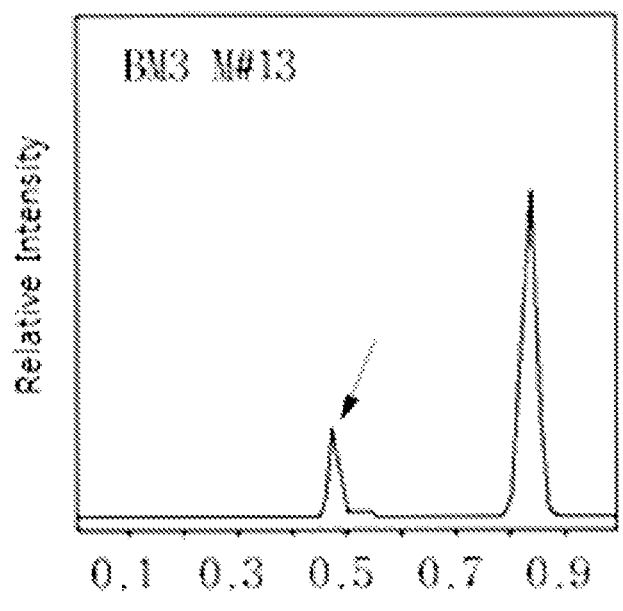
Figure 3F:
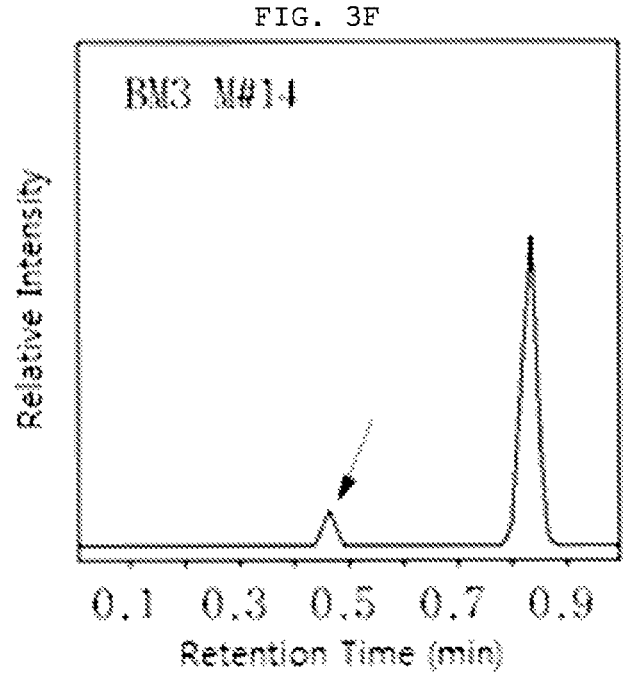
Figure 3G:
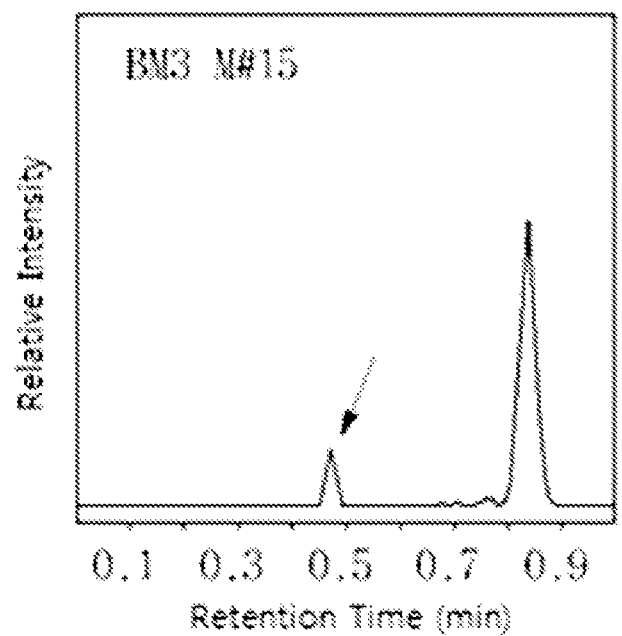
Figure 3H:
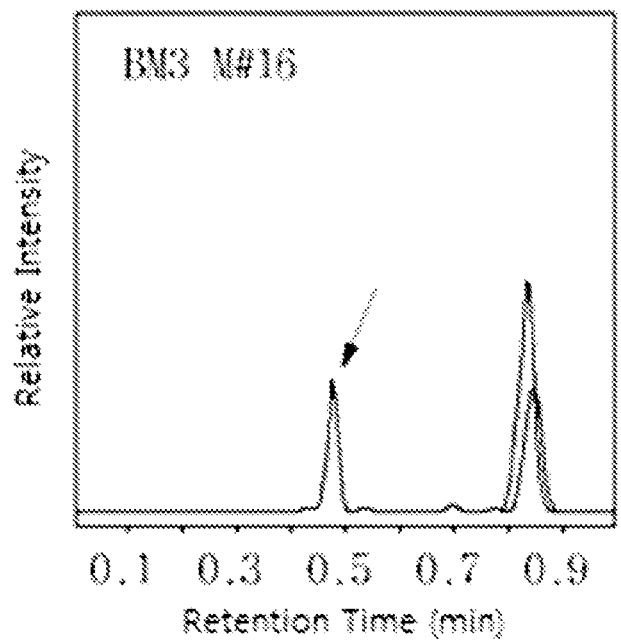
Figure 3I:
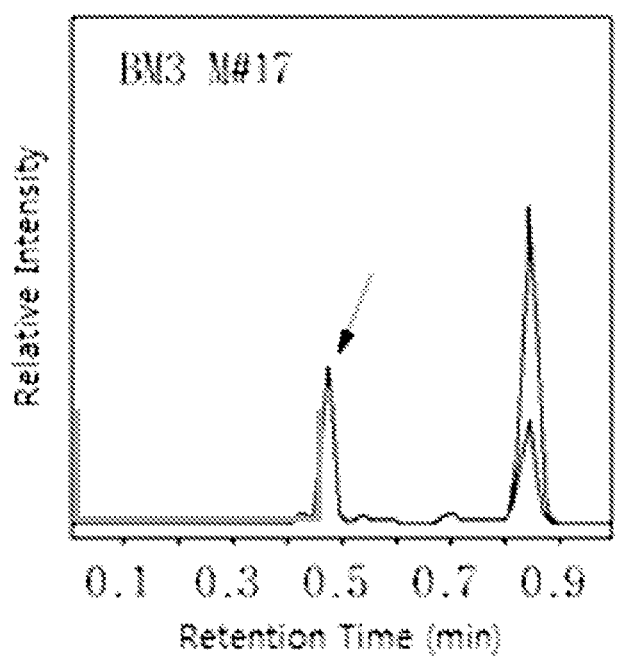
Figure 4A:
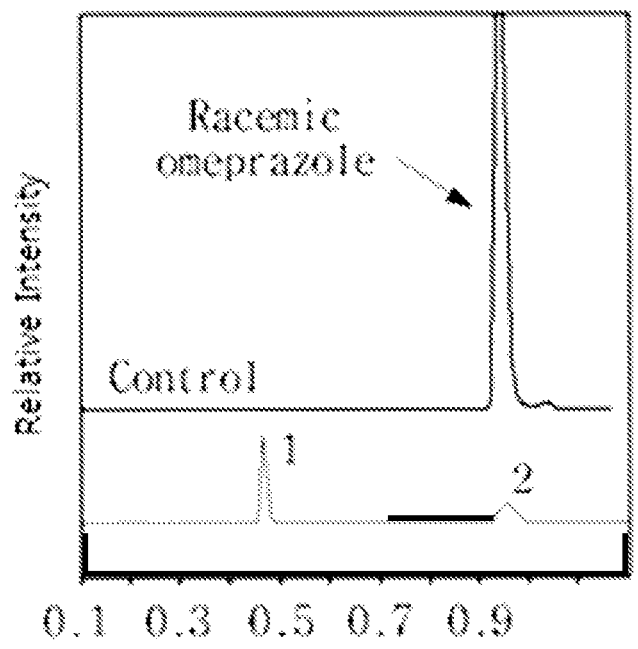
FIG. 4 shows HPLC chromatogram of an omeprazole metabolite derivative produced by a wild-type CYP102A1 mutant (#10) according to the present invention: (A) racemate, (B) R enantiomer and (C) S enantiomer.
Figure 4B:
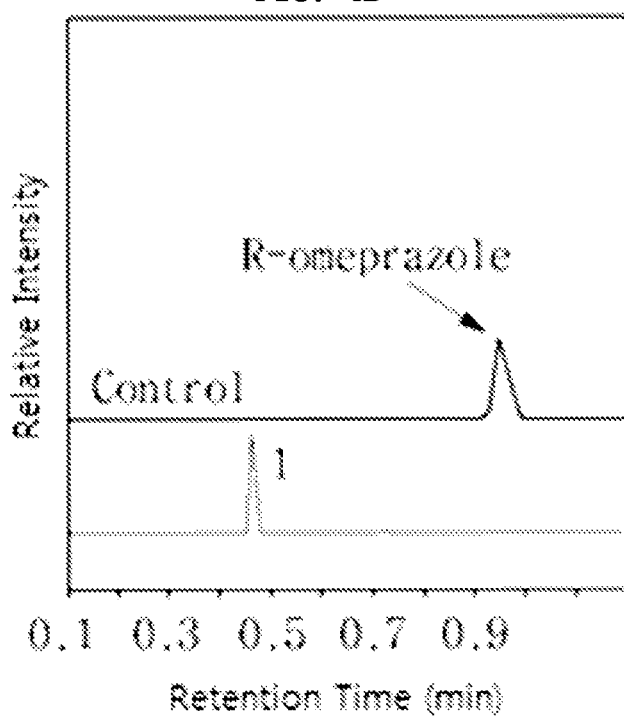

Hereinafter, embodiments of the present invention will be described in detail with reference to the accompanying drawings.

However, the detailed description is to help a specific understanding of the present invention, and the protection scope of the present invention is not limited to the following Examples.

Example 1

Construction of P450 BM3 Mutants by Site-Directed Mutagenesis 17 kinds of site-directed mutants of CYP102A1 were produced by a method as described by Kim et al., (see Drug Metab Dispos Vol. 35, pages 2166-2170, 2008). A primer used for introduction of a recognition site of BanHI/SacI and PCR primers for mutagenesis were shown in the following Table 1. A codon for amino acid substitution was expressed in italics and underlines. The PCR primers were purchased from Genotech Company (Daejeon, Korea). A gene encoding the mutants of CYP102A1 was amplified from pCWBM3 by a PCR method using a primer designed for promoting cloning with an expression vector pCWori (obtained by Dr. F. W. Dahlquist, University of California, Santa Barbara, Calif.) or pSE420 (Invitrogen).

Oligonucleotide assembly was practiced by using the 14 designed primer sets described in the following Table 1. The amplified gene was cloned with the BamHI/SacI recognition site of PCWBM3 BamHI/SacI vector. The plasmid transformed *Escherichia coli* DH5α F'-IQ (Invitrogen) and was used to express CYP102A1 mutant protein. After mutagenesis, whether or not desired mutation occurred was confirmed by DNA sequencing of Genotech Company (Daejeon).

TABLE 1

Primers Used for Mutants

| Name | Sequence |
|---|---|
| BamHI forward (SEQ ID NO: 1) | 5'-AGC *GGA TCC* ATG ACA ATT AAA GAA ATG CCT C-3' |
| SacI reverse (SEQ ID NO: 2) | 5'-ATC GAG CTC GTA GTT TGT AT-3' |
| R47L (SEQ ID NO: 3) | 5'-GCG CCT GGT *CTG* GTA ACG CG-3' |
| Y51F (SEQ ID NO: 4) | 5'-GTA ACG CGC *TTC* TTA TCA AGT-3' |
| E64G (SEQ ID NO: 5) | 5'-GCA TGC GAT *GGC* TCA CGC TTT-3' |
| A74G (SEQ ID NO: 6) | 5'-TA AGT CAA *GGC* CTT AAA TTT GTA CG-3' |
| F81I (SEQ ID NO: 7) | 5'-GTA CGT GAT *ATT* GCA GGA GAC-3' |
| L86I (SEQ ID NO: 8) | 5'-GGA GAC GGG *ATT* TTT ACA AGC T-3' |
| F87A (SEQ ID NO: 9) | 5'-GAC GGG TTA *GCG* ACA AGC TGG-3' |
| F87V (SEQ ID NO: 10) | 5'-GAC GGG TTA *GTG* ACA AGC TGG-3' |
| L143G (SEQ ID NO: 11) | 5'-GAA GTA CCG *GGC* GAC ATG ACA-3' |
| L188Q (SEQ ID NO: 12) | 5'-ATG AAC AAG *CAG* CAG CGA GCA A-3' |
| A264G (SEQ ID NO: 13) | 5'-TTC TTA ATT *GGG* GGA CAC GTG-3' |
| E267V (SEQ ID NO: 14) | 5'-T GCG GGA CAC *GTG* ACA ACA AGT-3' |
| L86I/F87V (SEQ ID NO: 15) | 5'-GGA GAC GGG *ATT GTG* ACA AGC TG-3' |

Example 2

Expression and Purification of Wild-Type CYP102A1 (pCWBM3) and Mutants Thereof

*Escherichia coli* DH5α F'-IQ was transformed with a plasmid containing genes of a wild-type CYP102A1 and mutants of CYP102A1 (see Kim et al., 2008b). An appropriate amount from one colony was inoculated into 5 me Luria-Bertani medium containing ampicillin (100 µg/ml) added thereto and then cultured at 37, the culture was inoculated into 250 ml Terrific Broth medium containing ampicillin (100 µl/ml) added thereto and cultured up to OD600 to 0.8 while shaking at with 250 rpm at 37° C., and isopropyl-β-D-thiogalactopyranoside was added thereto so as to have a final concentration of 0.5 mM, thereby inducing a gene expression. δ-aminolevulinic acid (0.1 mM) was added thereto. After the expression was induced, the culturing was additionally performed at 30° C. for 36 hours more, and centrifugation (15 minutes, 5000 g, 4° C.) was performed, thereby harvesting cells. The cell pellet was re-suspended with TES buffer (100 mM Tris-HCl, pH 7.6, 500 mM sucrose, 0.5 mM EDTA), and cells were lysed by sonication (sonicator; Misonix, Inc., Farmingdale, N.Y.). The cell lysate was centrifuged under conditions of 100,000 g, 90 minutes and 4° C. and soluble cytosolic fraction was collected to measure an activity. The cytosolic fraction was dialyzed into a 50 mM potassium phosphate buffer (pH 7.4) and stored at −80° C., and the fraction within one month after preparation was used for an experiment. The concentration of CYP102A1 was determined by CO-difference spectrum, wherein ε was 91 mM/cm. In both of the wild-type CYP102A1 and the mutants of CYP102A1, 300 to 700 nM P450 was generally obtained. An expression degree of the wild-type CYP102A1 and the mutants thereof had a range of 1.0 to 2.0 nmol P450/mg cell substrate protein. Among the produced mutants, the mutants having high catalyst activity with respect to several substrates in human were selected and the substituted domain of the amino acid in each mutant was shown in the following Table 2.

TABLE 2

| Abbreviations | BM3 wild type and mutants | Ref. |
|---|---|---|
| WT | BM3 wild type | |
| Mutant #1 | F87A | Carmichael et al., 2001 |
| Mutant #2 | A264G | Carmichael et al., 2001 |
| Mutant #3 | F87A/A264G | Carmichael et al., 2001 |
| Mutant #4 | R47L/Y51F | Carmichael et al., 2001 |
| Mutant #5 | R47L/Y51F/A264G | Carmichael et al., 2001 |
| Mutant #6 | R47L/Y51F/F87A | Carmichael et al., 2001 |
| Mutant #7 | R47L/Y51F/F87A/A264G | Carmichael et al., 2001 |
| Mutant #8 | A74G/F87V/L188Q | Li et al., 2001 |
| Mutant #9 | R47L/L86I/L188Q | Kim et al., 2008a |
| Mutant #10 | R47L/F87V/L188Q | van Vugt-Lussenburg et al., 2007 |
| Mutant #11 | R47L/F87V/L188Q/E267V | van Vugt-Lussenburg et al., 2007 |
| Mutant #12 | R47L/L86I/L188Q/E267V | Kim et al., 2008 |
| Mutant #13 | R47L/L86I/F87V/L188Q | van Vugt-Lussenburg et al., 2007 |
| Mutant #14 | R47L/F87V/E143G/L188Q/E267V | Kim et al., 2008a |
| Mutant #15 | R47L/E64G/F87V/E143G/L188Q/E267V | Kim et al., 2008a |
| Mutant #16 | R47L/F81I/F87V/E143G/L188Q/E267V | Kim et al., 2008a |
| Mutant #17 | R47L/E64G/F81I/F87V/E143G/L188Q/E267V | van Vugt-Lussenburg et al., 2007 |

Example 3

Oxidation of (Omeprazole by Wild-Type CYP102A1 or Mutant Thereof

Whether or not the wild-type CYP102A1 or mutants thereof was capable of oxidizing omeprazole was confirmed. CYP102A1 50 pmol and 100 µM substrates were put into 100 mM of a potassium phosphate buffer (pH 7.4) 0.25 me and were subjected to a typical steady state reaction. In order to initiate the reaction, an NADPH-generating system (final concentration: 10 mM glucose 6-phosphate, 0.5 mM NADP$^+$, and 1 IU yeast glucose 6-phosphate dehydrogenase per 1 me) was added. 20 mM omeprazole solution was prepared by DMSO, and diluted with an enzyme reaction solution so that an organic solvent has the final concentration of 1%(v/v) or less. For measuring an activity of human CYP2C19, 50 pmol P450, 100 pmol NADPH-P450 reductase (CPR), 100 pmol cytochrome b5 and 45 µM L-α-dilauroyl-sn-glycero-3-phosphocholine (DLPC) were used instead of 50 pmol CYP102A1. The reaction solution was reacted at 37 for 30 minutes, and the reaction was terminated by dichloromethane prepared in a cold state with twice amounts of ice.

(1) HPLC Analysis

The reaction mixture was centrifuged to remove the supernatant, the solvent thereof was evaporated under nitrogen gas (see Vickers et al., 1990), and the obtained mixture was analyzed by HPLC (see Piver et al., 2004). A sample (30 µl) was injected into Gemini C18 column (4.6 mm×150 mm, 5 µm, Phenomenex, Torrance, Calif.). 30% acetonitrile was used as a mobile phase. The mobile phase flowed at a rate of 1 ml/min and an eluent was measured by 302 nm of UV. In order to investigate whether or not CYP102A1 (P450 BM3) was capable of oxidizing omeprazole, the concentration of the substrate was fixed to 100 µM and oxidativity of omeprazole using the wild-type CYP102A1 and the mutants thereof was measured.

As a result, as confirmed in HPLC chromatogram of FIG. 3, it could be confirmed that a retention time of the peak of the produced metabolite was accurately the same as a retention time of the peak of a standard 5'-hydroxyomeprazole.

(2) LC-MS Analysis and NMR Analysis

In order to identify the omeprazole metabolites produced by CYP102A1 mutants, LC-MS analysis was conducted by comparison of LC profile and fragment pattern of the omeprazole and the metabolites. The CYP102A1 mutants and human CYP2C19 were reacted in the presence of 100 µM of omeprazole and the NADPH-generating system at 37° C. for 30 minutes. The reaction was terminated by adding twice amount of $CH_2Cl_2$ cooled by ice. After centrifugation, the supernatant was removed and discarded and an organic solvent layer was dried in the presence of nitrogen. The reactant was re-constituted into a vortex mixing with 100 µl of the mobile phase and was subjected to sonication for 20 seconds. An appropriate amount 5 µl of the prepared solution was injected into an LC column.

The LC-MS analysis was conducted by Shimadzu LCMS-2010 EV system (Shimadzu, Kyoto, Japan) having an LC-MS software mounted therein with an electro spray ionization (positive) mode. In the Shim-pack VP-ODS column (250 mm×2.0 mm i.d.; Shimadzu co., Japan), 30% acetonitrile was used as a mobile phase. The mobile phase was separated with a flow velocity of 0.1 ml/min. In order to confirm the metabolite, mass spectra were recorded with electro spray ionization (positive) mode. An interface and a detector volt were 4.4 kV and 1.5 kV, respectively. A nebulization gas flow rate was set to be 1.5 ml/min, an interface, a curve desolvation line (CDL)

and a heat-block temperature were 250, 250 and 200° C., respectively. Total ion current (TIC) profiles of the metabolites produced by CYP102A1 mutant #10 and human CYP2C19 were investigated.

As a result, as shown in FIG. 6, the mass spectra of the reaction sample shows peaks at 6.200 min (5'-hydroxyomeprazole) and 15.267 min (omeprazole), and when calculating the mass spectra of the 5'-hydroxyl product and the omeprazole by CYP102A1 mutant #10 into [M+H]$^+$, the observed values were 362 and 346, respectively.

In addition, the LC-MS analysis of the reaction mixture confirmed that 5'-hydroxyomeprazole was produced by the CYP102A1 mutant. It was confirmed that the retention time and the fragment pattern of the CYP102A1 metabolite was accurately the same as those of authentic metabolites produced by human CYP2C19.

Figure 8A:
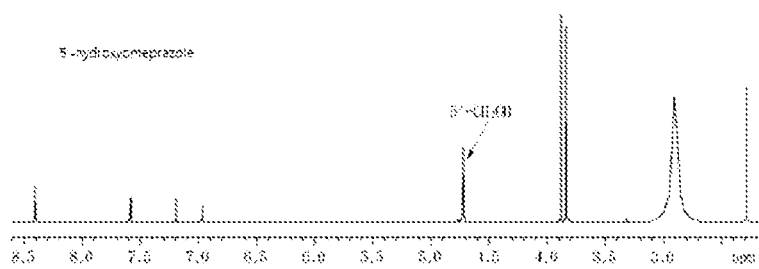
FIG. 8 shows a structure of the omeprazole metabolite produced by the CYP102A1 mutant (#10) according to the present invention observed by nuclear magnetic resonance (NMR) spectroscopy: (A) 5-hydroxyomeprazole and (B) omeprazole.
Figure 8B:
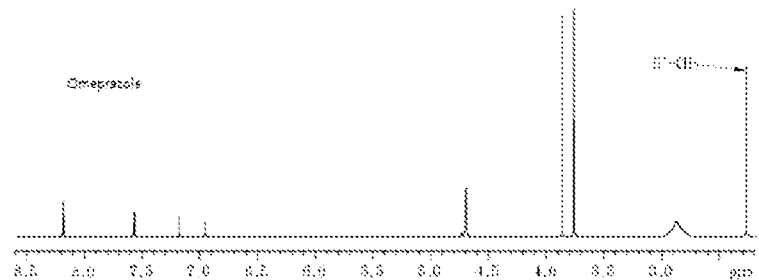

As a result obtained by analyzing the structure of the metabolite produced by the bacterial CYP102A1 mutant #10 by an NMR analysis method, as shown in FIG. 8, it could be confirmed that the produced product was not 3'-hydroxyomeprazole but 5'-hydroxyomeprazole.

(3) Determination of Turnover Number

A production rate of the omeprazole oxides by the wild-type CYP102A1 and the mutants thereof was confirmed. 100 μM omeprazole was used, the NADPH-generating system was added to initiate the reaction, and the reaction was performed at 37° C. for 30 minutes to determine a turnover number. The production rate of the omeprazole was determined by HPLC as described above.

Figure 5:
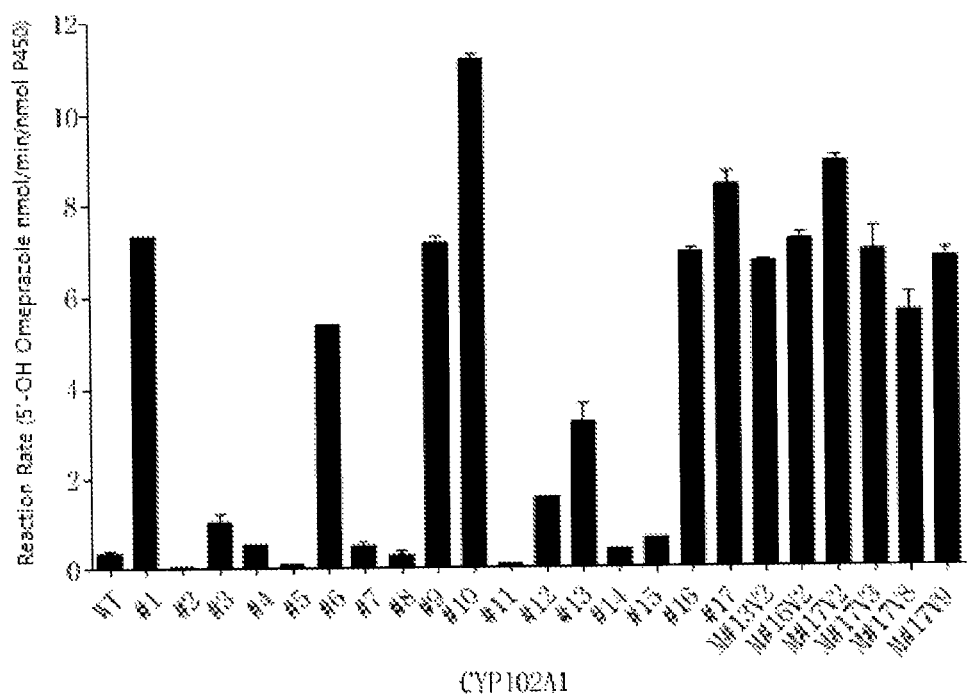
FIG. 5 shows a production rate of an oxide of omeprazole by the wild-type CYP102A1 and the mutant thereof according to the present invention.
Figure 6A:
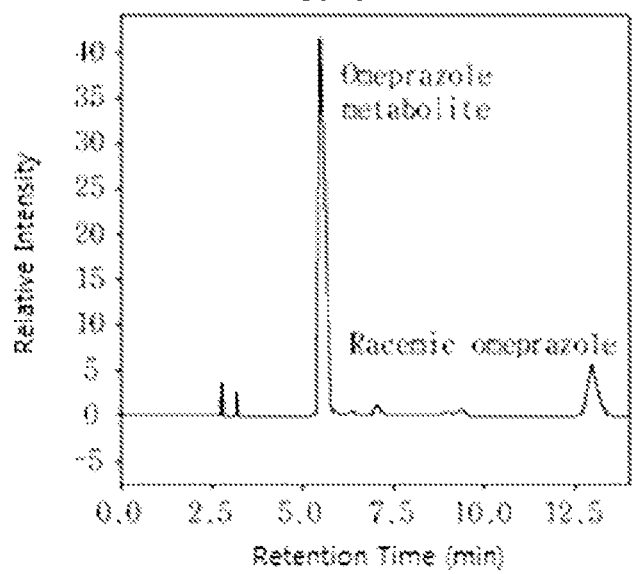
FIG. 6 shows LC-MS elution profile of omeprazoles produced by human CYP2C19 and the CYP102A1 mutant (#10) according to the present invention, and a metabolite thereof: (A)-(C) CYP102A1 mutant #10, (D)-(F): human CYP2C19).
Figure 6B:
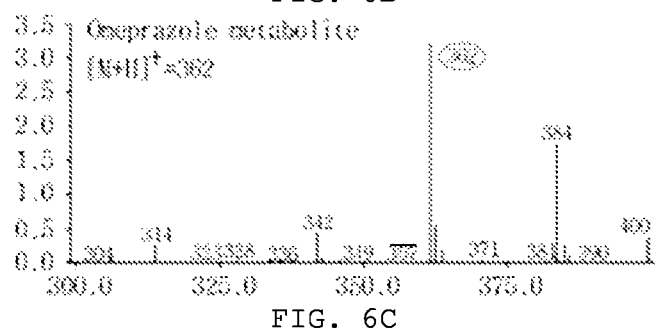
Figure 6C:
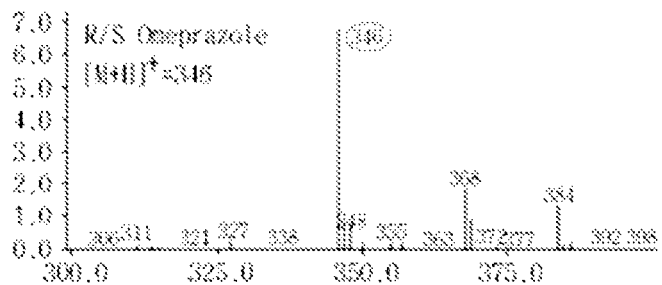
Figure 6D:
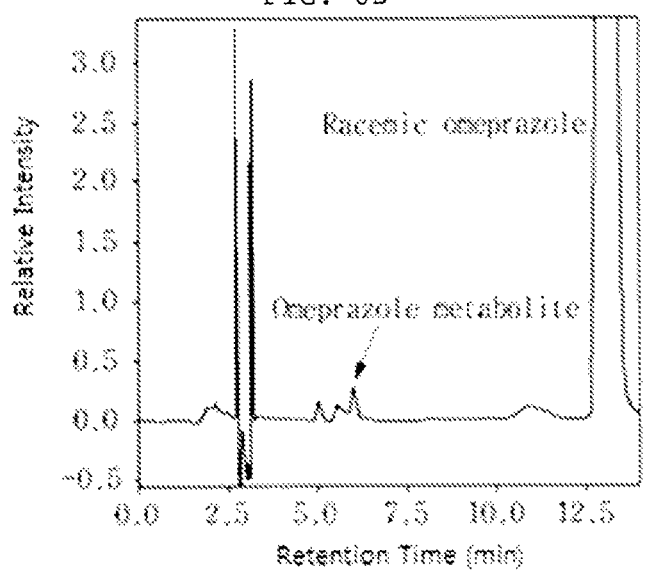
Figure 6E:
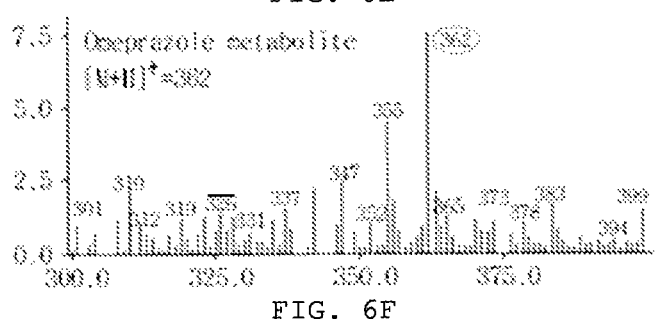
Figure 6F:
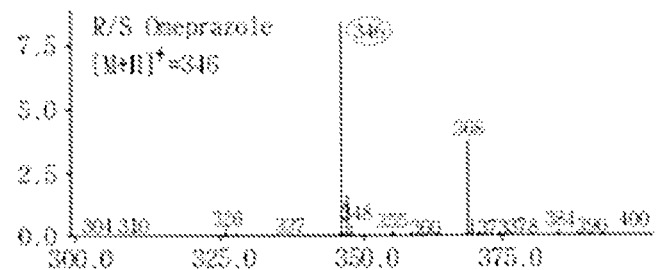

It could be confirmed from the results of FIG. 5 that the turnover number of the wild-type CYP102A1, 17 kinds of mutants thereof, and 6 kinds of mutant kimeras varied at a large range. In addition, the total turnover number (TTNs) (mol product/mol catalyst) of the CYP102A1 mutant was investigated. In order to measure TTNs of the CYP102A1 mutant, 0.1 mM to 2 mM omeprazole was used, and the reaction was performed with an interval from 30 minutes up to 5 hours. The production rate of the omeprazole metabolite was determined by HPLC.

Figure 7A:
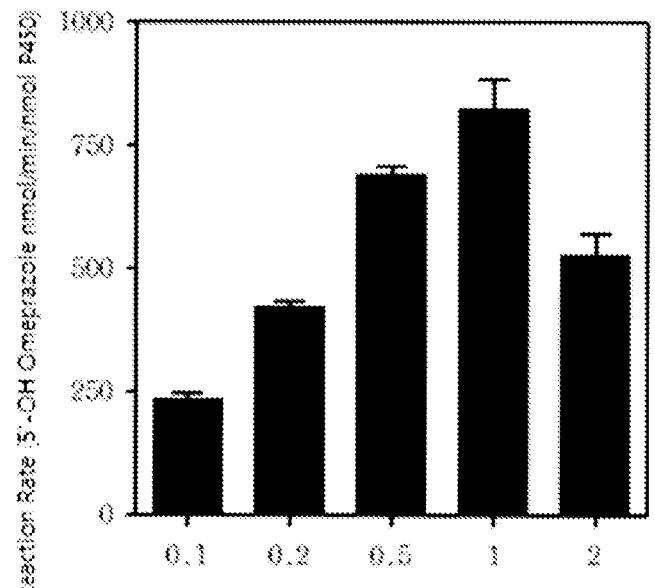
FIG. 7 shows total molecular catalytic activity of a 5'-hydroxyl product produced by the CYP102A1 mutant (#10) of the present invention depending on concentration (A) and treated time (B) of the omeprazole.
Figure 7B:
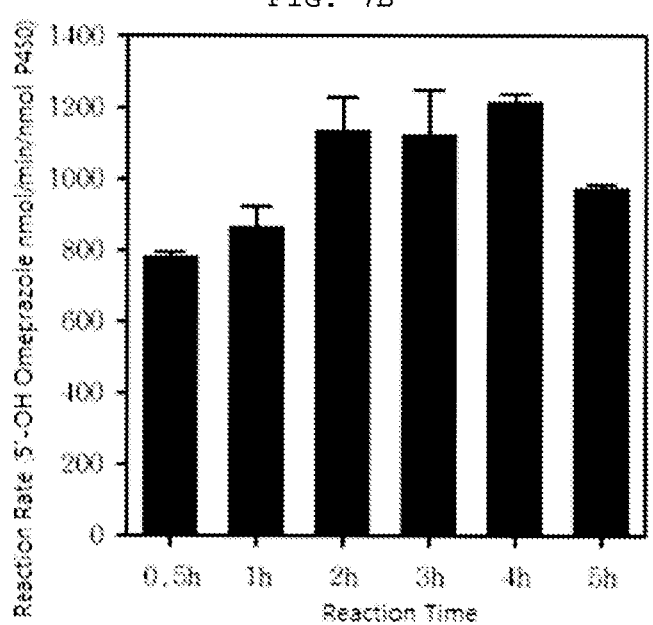

As a result, as shown in FIG. 7, it could be confirmed that the CYP102A1 mutant #10 showing high activity in TTNs had the highest activity when the reaction was performed for 2 to 4 hours with 1 mM omeprazole; meanwhile, the wild-type CYP102A1 enzyme hardly had an activity with respect to omeprazole. Production of the omeprazole metabolites by chemical synthesis has not been reported yet. It means that the production of the omeprazole metabolites using the CYP102A1 enzyme is an alternative of the chemical synthesis of the metabolites.

It could be confirmed from the results above that a 5'-OH product which is a human metabolite was produced by catalyzing the same reaction as human CYP2C19 by the bacterial CYP102A1 enzymes. It could be confirmed that the oxidation of the omeprazole which is a human P450 substrate was catalyzed by the wild-type CYP102A1 and the mutants thereof, and the hydroxyl product, that is, the 5'-OH product as a main metabolite was produced, and the production of the produced metabolites was confirmed by comparison with the product produced by the human CYP2C19 by HPLC and LC-MS.

From the above-described results, it could be confirmed that the CYP102A1 mutants are capable of effectively producing the metabolites in human from omeprazole, wherein the metabolites may be used to evaluate efficacy, toxicity, pharmacokinetics, and the like, of the drug, in drug development, and may be used to produce metabolite derivatives in human, which will be a lead compound in the drug development.

The invention claimed is:

1. A mutant of CYP102A1, wherein the mutant of CYP102A1 has mutations R48L, F88V and L189Q based on SEQ ID NO: 16 of the wild-type CYP102A1.

2. A composition for producing a 5'-hydroxyl product from omeprazole, containing a mutant of enzyme CYP102A1, wherein wild-type CYP102A1 comprises the amino acid sequence of SEQ ID NO: 16, and wherein the mutant of CYP102A1 has mutations R48L, F88V and L189Q based on SEQ ID NO: 16.

3. The composition of claim 2, wherein the omeprazole is a racemate containing S- or R-omeprazole which is an enantiomer, or an enantiomer of the S- and R-omeprazole at a ratio of 50:50.

4. A kit for producing a 5'-hydroxyl product from omeprazole, comprising an NADPH-generating system and a mutant of CYP102A1, wherein the mutant of CYP102A1 has mutations on the sequence of a wild-type CYP102A1, said wild-type CYP102A1 comprising the amino acid sequence of SEQ ID NO: 16, and wherein the mutations comprise R48L, F88V and L189Q based on SEQ ID NO: 16.

5. The kit of claim 4, wherein the NADPH-generating system contains glucose 6-phosphate, $NADP^+$ and yeast glucose-6-phosphate dehydrogenase.

6. A method for producing a 5'-hydroxyl product from omeprazole, including reacting the omeprazole with a mutant of enzyme CYP102A1, wherein a wild-type CYP102A1 comprises the amino acid sequence of SEQ ID NO: 16, and wherein the mutant of CYP102A1 has mutations R48L, F88V and L189Q based on SEQ ID NO: 16.

7. The method of claim 6, further comprising: adding an NADPH-generating system.

* * * * *

SEQUENCE LISTING

```
<160> NUMBER OF SEQ ID NOS: 19

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agcggatcca tgacaattaa agaaatgcct c                                       31

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atcgagctcg tagtttgtat                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 3
gcgcctggtc tggtaacgcg                                                                          20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtaacgcgct tcttatcaag t                                                                        21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcatgcgatg gctcacgctt t                                                                        21

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
taagtcaagg ccttaaattt gtacg                                                                    25

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtacgtgata ttgcaggaga c                                                                        21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggagacggga tttttacaag ct                                                                       22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 9
gacgggttag cgacaagctg g                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gacgggttag tgacaagctg g                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaagtaccgg gcgacatgac a                                              21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atgaacaagc agcagcgagc aa                                             22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttcttaattg ggggacacgt g                                              21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgcgggacac gtgacaacaa gt                                             22

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 15
ggagacggga ttgtgacaag ctg                                           23

<210> SEQ ID NO 16
<211> LENGTH: 1049
<212> TYPE: PRT
<213> ORGANISM: Unknown
<220> FEATURE:
<223> OTHER INFORMATION: Description of Unknown: Bacterial cytochrome
      P450 BM3 (CYP102A1) sequence

<400> SEQUENCE: 16

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
                930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
                995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 17
<211> LENGTH: 3150
<212> TYPE: DNA
<213> ORGANISM: Unknown
<220> FEATURE:
<223> OTHER INFORMATION: Description of Unknown: Bacterial cytochrome
      P450 BM3 (CYP102A1) sequence

<400> SEQUENCE: 17
atgacaatta aagaaatgcc tcagccaaaa acgtttggag agcttaaaaa tttaccgtta     60
ttaaacacag ataaaccggt tcaagctttg atgaaaattg cggatgaatt aggagaaatc    120
tttaaattcg aggcgcctgg tcgtgtaacg cgctacttat caagtcagcg tctaattaaa    180
gaagcatgcg atgaatcacg ctttgataaa aacttaagtc aagcgcttaa atttgtacgt    240
gattttgcag gagacgggtt atttacaagc tggacgcatg aaaaaaattg gaaaaaagcg    300
cataatatct tacttccaag cttcagtcag caggcaatga aaggctatca tgcgatgatg    360

```
gtcgatatcg ccgtgcagct tgttcaaaag tgggagcgtc taaatgcaga tgagcatatt      420
gaagtaccgg aagacatgac acgtttaacg cttgatacaa ttggtctttg cggctttaac      480
tatcgcttta acagctttta ccgagatcag cctcatccat ttattacaag tatggtccgt      540
gcactggata agcaatgaa caagctgcag cgagcaaatc cagacgaccc agcttatgat       600
gaaaacaagc gccagtttca agaagatatc aaggtgatga acgacctagt agataaaatt      660
attgcagatc gcaaagcaag cggtgaacaa agcgatgatt tattaacgca tatgctaaac      720
ggaaaagatc cagaaacggg tgagccgctt gatgacgaga acattcgcta tcaaattatt      780
acattcttaa ttgcgggaca cgaaacaaca agtggtcttt tatcatttgc gctgtatttc      840
ttagtgaaaa atccacatgt attacaaaaa gcagcagaag aagcagcacg agttctagta      900
gatcctgttc caagctacaa acaagtcaaa cagcttaaat atgtcggcat ggtcttaaac      960
gaagcgctgc gcttatggcc aactgctcct gcgttttccc tatatgcaaa agaagatacg     1020
gtgcttggag gagaatatcc tttagaaaaa ggcgacgaac taatggttct gattcctcag     1080
cttcaccgtg ataaaacaat ttggggagac gatgtggaag agttccgtcc agagcgtttt     1140
gaaaatccaa gtgcgattcc gcagcatgcg tttaaaccgt ttggaaacgg tcagcgtgcg     1200
tgtatcggtc agcagttcgc tcttcatgaa gcaacgctgg tacttggtat gatgctaaaa     1260
cactttgact tgaagatca tacaaactac gagctcgata ttaaagaaac tttaacgtta      1320
aaacctgaag gctttgtggt aaaagcaaaa tcgaaaaaaa ttccgcttgg cggtattcct     1380
tcacctagca ctgaacagtc tgctaaaaaa gtacgcaaaa aggcagaaaa cgctcataat     1440
acgccgctgc ttgtgctata cggttcaaat atgggaacag ctgaaggaac ggcgcgtgat     1500
ttagcagata ttgcaatgag caaaggatt gcaccgcagg tcgcaacgct tgattcacac      1560
gccggaaatc ttccgcgcga aggagctgta ttaattgtaa cggcgtctta taacggtcat     1620
ccgcctgata acgcaaagca atttgtcgac tggttagacc aagcgtctgc tgatgaagta     1680
aaaggcgttc gctactccgt atttggatgc ggcgataaaa actgggctac tacgtatcaa     1740
aaagtgcctg ctttttatcga tgaaacgctt gccgctaaag gggcagaaaa catcgctgac     1800
cgcggtgaag cagatgcaag cgacgacttt gaaggcacat atgaagaatg gcgtgaacat     1860
atgtggagtg acgtagcagc ctactttaac ctcgacattg aaaacagtga agataataaa     1920
tctactcttt cacttcaatt tgtcgacagc gccgcggata tgccgcttgc gaaaatgcac     1980
ggtgcgtttt caacgaacgt cgtagcaagc aaagaacttc aacagccagg cagtgcacga     2040
agcacgcgac atcttgaaat tgaacttcca aaagaagctt cttatcaaga aggagatcat     2100
ttaggtgtta ttcctcgcaa ctatgaagga atagtaaacc gtgtaacagc aaggttcggc     2160
ctagatgcat cacagcaaat ccgtctggaa gcagaagaag aaaaattagc tcatttgcca     2220
ctcgctaaaa cagtatccgt agaagagctt ctgcaatacg tggagcttca agatcctgtt     2280
acgcgcacgc agcttcgcgc aatggctgct aaaacggtct gcccgccgca taaagtagag     2340
cttgaagcct tgcttgaaaa gcaagcctac aaagaacaag tgctggcaaa acgtttaaca     2400
atgcttgaac tgcttgaaaa atacccggcg tgtgaaatga aattcagcga atttatcgcc     2460
cttctgccaa gcatacgccc gcgctattac tcgatttctt catcacctcg tgtcgatgaa     2520
aaacaagcaa gcatcacggt cagcgttgtc tcaggagaag cgtggagcgg atatggagaa     2580
tataaaggaa ttgcgtcgaa ctatcttgcc gagctgcaag aaggagatac gattacgtgc     2640
tttatttcca caccgcagtc agaatttacg ctgccaaaag accctgaaac gccgcttatc     2700
atggtcggac cgggaacagg cgtcgcgccg tttagaggct ttgtgcaggc gcgcaaacag     2760
```

```
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaggc     3120 cgatacgcaa aagacgtgtg ggctgggtaa                                     3150
```

<210> SEQ ID NO 18
<211> LENGTH: 1049
<212> TYPE: PRT
<213> ORGANISM: Unknown
<220> FEATURE:
<223> OTHER INFORMATION: Description of Unknown: Bacterial cytochrome
      P450 BM3 (CYP102A1) mutant sequence

<400> SEQUENCE: 18

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Gln Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285
```

-continued

```
Gln Lys Ala Ala Glu Glu Ala Ala Arg Val Leu Val Asp Pro Val Pro
    290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
            340                 345                 350
Glu Leu Met Val Leu Ile Pro Gln Leu His Arg Asp Lys Thr Ile Trp
        355                 360                 365
Gly Asp Asp Val Glu Glu Phe Arg Pro Glu Arg Phe Glu Asn Pro Ser
370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
        435                 440                 445
Ala Lys Ser Lys Lys Ile Pro Leu Gly Gly Ile Pro Ser Pro Ser Thr
450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
        515                 520                 525
Ala Val Leu Ile Val Thr Ala Ser Tyr Asn Gly His Pro Pro Asp Asn
530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
        595                 600                 605
Asp Phe Glu Gly Thr Tyr Glu Glu Trp Arg Glu His Met Trp Ser Asp
610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
            660                 665                 670
Leu Gln Gln Pro Gly Ser Ala Arg Ser Thr Arg His Leu Glu Ile Glu
        675                 680                 685
Leu Pro Lys Glu Ala Ser Tyr Gln Glu Gly Asp His Leu Gly Val Ile
690                 695                 700
```

```
Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
            805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
            885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
            965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
    1010            1015            1020

Val Ser Glu Ala Asp Ala Arg Leu Trp Leu Gln Gln Leu Glu Glu
    1025            1030            1035

Lys Gly Arg Tyr Ala Lys Asp Val Trp Ala Gly
    1040            1045

<210> SEQ ID NO 19
<211> LENGTH: 1049
<212> TYPE: PRT
<213> ORGANISM: Unknown
<220> FEATURE:
<223> OTHER INFORMATION: Description of Unknown: Bacterial cytochrome
      P450 BM3 (CYP102A1) mutant sequence
<220> FEATURE:
<221> NAME/KEY: MOD_RES
<222> LOCATION: (48)..(48)
<223> OTHER INFORMATION: Arg or Leu
```

```
<220> FEATURE:
<221> NAME/KEY: MOD_RES
<222> LOCATION: (88)..(88)
<223> OTHER INFORMATION: Phe or Val
<220> FEATURE:
<221> NAME/KEY: MOD_RES
<222> LOCATION: (189)..(189)
<223> OTHER INFORMATION: Leu or Gln

<400> SEQUENCE: 19

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Xaa
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Xaa Thr Ser Trp Thr His Glu Lys Asn
                85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Val
            115                 120                 125

Gln Lys Trp Glu Arg Leu Asn Ala Asp Glu His Ile Glu Val Pro Glu
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Xaa Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
            245                 250                 255

Tyr Gln Ile Ile Thr Phe Leu Ile Ala Gly His Glu Thr Thr Ser Gly
        260                 265                 270

Leu Leu Ser Phe Ala Leu Tyr Phe Leu Val Lys Asn Pro His Val Leu
            275                 280                 285

Gln Lys Ala Ala Glu Glu Ala Ala Arg Val Leu Val Asp Pro Val Pro
        290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
            325                 330                 335

Lys Glu Asp Thr Val Leu Gly Gly Glu Tyr Pro Leu Glu Lys Gly Asp
        340                 345                 350

Glu Leu Met Val Leu Ile Pro Gln Leu His Arg Asp Lys Thr Ile Trp
            355                 360                 365
```

-continued

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
770                 775                 780

```
Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
            805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
            885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
            965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010        1015                1020

Val Ser Glu Ala Asp Ala Arg Leu Trp Leu Gln Gln Leu Glu Glu
    1025        1030                1035

Lys Gly Arg Tyr Ala Lys Asp Val Trp Ala Gly
    1040        1045
```